(12) United States Patent
Iverson

(10) Patent No.: US 8,765,656 B2
(45) Date of Patent: Jul. 1, 2014

(54) DISINFECTING/MINERAL TREATING COMPOSITION AND METHODS COMPRISING A CHLORITE OR CHLORATE SALT

(71) Applicant: Carl E. Iverson, Olympia, WA (US)

(72) Inventor: Carl E. Iverson, Olympia, WA (US)

(73) Assignee: CH2O Incorporated, Olympia, WA (US)

( * ) Notice: Subject to any disclaimer, the term of this patent is extended or adjusted under 35 U.S.C. 154(b) by 0 days.

(21) Appl. No.: 13/645,362

(22) Filed: Oct. 4, 2012

(65) Prior Publication Data

US 2013/0233696 A1    Sep. 12, 2013

Related U.S. Application Data

(62) Division of application No. 11/498,495, filed on Aug. 2, 2006, now Pat. No. 8,513,176.

(51) Int. Cl.
*C11D 9/34* (2006.01)
*C11D 3/395* (2006.01)

(52) U.S. Cl.
USPC ........... 510/247; 510/199; 510/218; 510/219; 510/236; 510/367; 510/379; 510/380; 510/382; 510/436; 510/467

(58) Field of Classification Search
USPC ......... 510/199, 218, 219, 236, 247, 367, 379, 510/380, 382, 436, 467
See application file for complete search history.

(56) References Cited

U.S. PATENT DOCUMENTS

| | | | |
|---|---|---|---|
| 1,488,097 A | 3/1924 | Creger | |
| 2,944,967 A | 7/1960 | Dunklin et al. | |
| 3,149,151 A | 9/1964 | Schiefer et al. | |
| 3,150,081 A | 9/1964 | Haslam et al. | |
| 3,214,454 A | 10/1965 | Blaser et al. | |
| 3,591,515 A | 7/1971 | Lovely | |
| 3,702,298 A | 11/1972 | Zsoldos et al. | |
| 3,814,820 A | 6/1974 | Busta et al. | |
| 3,869,559 A | 3/1975 | Clark | |
| 3,892,563 A | 7/1975 | La Point | |
| 4,001,443 A | 1/1977 | Dave | |
| 4,021,585 A | 5/1977 | Svoboda et al. | |
| 4,089,796 A | 5/1978 | Harris et al. | |
| 4,108,772 A | 8/1978 | Alexander | |
| 4,143,115 A | 3/1979 | Ward et al. | |
| 4,247,051 A | 1/1981 | Allport | |
| 4,261,837 A | 4/1981 | West, Jr. et al. | |
| 4,292,292 A | 9/1981 | Hicks et al. | |
| 4,339,468 A | 7/1982 | Kielsmeier | |
| 4,451,444 A | 5/1984 | Santillie et al. | |
| 4,486,581 A | 12/1984 | Walinsky | |
| 4,497,713 A | 2/1985 | Geiger | |
| 4,534,866 A | 8/1985 | Becker | |
| 4,534,952 A | 8/1985 | Rapson et al. | |
| 4,568,463 A | 2/1986 | Klein | |
| 4,574,084 A * | 3/1986 | Berger | 424/601 |
| 4,590,057 A | 5/1986 | Hicks | |
| 4,610,783 A | 9/1986 | Hudson | |
| 4,618,719 A | 10/1986 | Bay et al. | |
| 4,649,025 A | 3/1987 | Hwa et al. | |
| 4,689,169 A | 8/1987 | Mason et al. | |
| 4,690,772 A | 9/1987 | Tell et al. | |
| 4,693,832 A | 9/1987 | Hurst | |
| 4,731,193 A | 3/1988 | Mason et al. | |
| 4,759,852 A * | 7/1988 | Trulear | 210/699 |
| 4,802,990 A | 2/1989 | Inskeep, Jr. | |
| 4,850,531 A | 7/1989 | Littleton | |
| 4,889,654 A | 12/1989 | Mason et al. | |
| 4,913,822 A | 4/1990 | Chen et al. | |
| 4,925,645 A | 5/1990 | Mason | |
| 5,002,746 A | 3/1991 | Norell | |
| 5,008,096 A | 4/1991 | Ringo et al. | |
| 5,009,875 A | 4/1991 | Kelley et al. | |
| 5,047,078 A | 9/1991 | Gill | |
| 5,072,022 A | 12/1991 | Bakos et al. | |
| 5,084,210 A | 1/1992 | Teeters | |
| 5,091,562 A * | 2/1992 | Immenkeppel et al. | 562/24 |
| 5,106,406 A | 4/1992 | Sylling et al. | |
| 5,112,521 A * | 5/1992 | Mullins et al. | 252/180 |
| 5,126,070 A | 6/1992 | Leifheit et al. | |
| 5,130,052 A | 7/1992 | Kreh et al. | |
| 5,171,477 A | 12/1992 | Kreh | |
| 5,173,258 A | 12/1992 | Childers | |
| 5,204,081 A | 4/1993 | Mason et al. | |
| 5,208,031 A | 5/1993 | Kelly | |
| 5,226,972 A | 7/1993 | Bell | |
| 5,304,236 A | 4/1994 | Fears | |

(Continued)

FOREIGN PATENT DOCUMENTS

| | | |
|---|---|---|
| EP | 0006065 | 12/1979 |
| EP | 0017373 | 10/1980 |

(Continued)

OTHER PUBLICATIONS

3 Sheets from Unocal Agriproducts Advertising, Unocal 76, P.O. Box 60455, Los Angles, CA 90060, 1992 & 1994.

(Continued)

*Primary Examiner* — Charles Boyer

(74) *Attorney, Agent, or Firm* — Fish & Richardson P.C.

(57) ABSTRACT

Source water is treated by mixing a first component selected from the group comprising neutralized phosphonic acid compounds, neutralized phosphonate compounds, neutralized derivatives of phosphorus, neutralized anti-scalent polymers, and mixtures thereof, a second component from the group comprising chlorite salt and chlorate salt is admixed to the mixture of the water and the first component, and water. The water and the first and second components are present in amounts sufficient to form a stable liquid composition in which there is substantially no conversion of the second component to chlorine dioxide.

21 Claims, 2 Drawing Sheets

(56) References Cited

U.S. PATENT DOCUMENTS

| | | |
|---|---|---|
| 5,314,629 A | 5/1994 | Griese et al. |
| 5,320,779 A | 6/1994 | Fivizzani |
| 5,324,477 A | 6/1994 | Schroeder et al. |
| 5,332,580 A | 7/1994 | Young et al. |
| 5,360,550 A | 11/1994 | Clubley et al. |
| 5,369,099 A | 11/1994 | Iverson, Jr. et al. |
| 5,389,390 A | 2/1995 | Kross |
| 5,401,419 A | 3/1995 | Kocib |
| 5,405,549 A | 4/1995 | Pitochelli |
| 5,411,666 A | 5/1995 | Hollis et al. |
| 5,422,348 A | 6/1995 | Iverson, Jr. et al. |
| 5,424,032 A | 6/1995 | Christensen et al. |
| 5,451,266 A | 9/1995 | Kirk et al. |
| 5,547,612 A | 8/1996 | Austin et al. |
| 5,618,440 A | 4/1997 | Mason |
| 5,799,833 A | 9/1998 | Green et al. |
| 5,858,443 A | 1/1999 | Hei et al. |
| 5,863,584 A | 1/1999 | Thomas, Jr. et al. |
| 5,930,950 A | 8/1999 | Iverson, Jr. et al. |
| 5,941,635 A | 8/1999 | Stewart |
| 5,997,602 A | 12/1999 | Aijala |
| 6,004,604 A | 12/1999 | Thomas, Jr. et al. |
| 6,017,864 A * | 1/2000 | Brittain et al. ............... 510/218 |
| 6,036,740 A | 3/2000 | Miller et al. |
| 6,077,480 A | 6/2000 | Edwards et al. |
| 6,083,457 A | 7/2000 | Parkinson et al. |
| 6,096,226 A | 8/2000 | Fuchs et al. |
| 6,120,731 A | 9/2000 | Kross et al. |
| 6,238,573 B1 | 5/2001 | Miller et al. |
| 6,281,278 B1 | 8/2001 | Takase et al. |
| 6,291,411 B1 | 9/2001 | Callaghan et al. |
| 6,325,970 B1 | 12/2001 | Parkinson et al. |
| 6,345,632 B1 | 2/2002 | Ludwig et al. |
| 6,350,410 B1 | 2/2002 | Iverson et al. |
| 6,362,152 B1 | 3/2002 | Young et al. |
| 6,428,696 B2 * | 8/2002 | Kuke ............................ 210/192 |
| 6,767,470 B2 | 7/2004 | Iverson et al. |
| 6,840,251 B2 * | 1/2005 | Gill et al. .................. 134/22.12 |
| 6,852,348 B2 | 2/2005 | Iverson et al. |
| 6,881,320 B1 | 4/2005 | Krafton et al. |
| 7,033,510 B2 | 4/2006 | Cilliers et al. |
| 7,186,376 B2 | 3/2007 | Iverson et al. |
| 7,252,769 B2 | 8/2007 | Dickinson |
| 7,266,924 B2 | 9/2007 | Van De Lande |
| 7,601,266 B2 | 10/2009 | Iverson |
| 2001/0009897 A1 | 7/2001 | Bauer et al. |
| 2002/0014463 A1 | 2/2002 | Iverson et al. |
| 2002/0061236 A1 | 5/2002 | Inoue |
| 2002/0061263 A1 | 5/2002 | Taylor |
| 2003/0139310 A1 | 7/2003 | Smith et al. |
| 2003/0200997 A1 | 10/2003 | Gill et al. |
| 2003/0216271 A1* | 11/2003 | Scheper et al. ............... 510/220 |
| 2005/0075263 A1 | 4/2005 | Gomez |
| 2005/0217176 A1 | 10/2005 | Van De Lande |
| 2006/0054563 A1 | 3/2006 | Tsuneki et al. |
| 2006/0089285 A1* | 4/2006 | Ahmed et al. ............... 510/370 |
| 2006/0153766 A1 | 7/2006 | Iverson et al. |
| 2007/0117215 A1 | 5/2007 | Davis et al. |
| 2008/0032905 A1 | 2/2008 | Iverson |
| 2008/0258104 A1 | 10/2008 | Mullins et al. |
| 2009/0294381 A1 | 12/2009 | Coffey et al. |
| 2009/0298689 A1 | 12/2009 | Iverson |
| 2010/0086514 A1 | 4/2010 | Liu et al. |

FOREIGN PATENT DOCUMENTS

| | | |
|---|---|---|
| EP | 0225051 | 6/1987 |
| EP | 154449 | 7/1989 |
| EP | 0380171 | 8/1990 |
| ES | 2043238 | 12/1993 |
| ES | 2315167 | 3/2009 |
| GB | 746615 | 3/1956 |
| HU | 38594 | 6/1986 |
| HU | 0251955 | 1/1988 |
| JP | 8283112 | 10/1996 |
| JP | 971502 | 3/1997 |
| JP | 11130407 | 5/1999 |
| MX | 20007000550 | 2/2009 |
| PL | 557287 | 3/1993 |
| WO | 9523510 | 9/1995 |
| WO | WO9625049 | 8/1996 |
| WO | WO9632523 | 10/1996 |
| WO | 9733477 | 9/1997 |
| WO | 9800012 | 1/1998 |
| WO | 0048470 | 8/2000 |
| WO | WO0158262 | 8/2001 |
| WO | WO0212130 | 2/2002 |

OTHER PUBLICATIONS

"Broadening the Scope of Chlorine Dioxide Technology" (brochure), Rio Linda Chemical Co., Inc.

"Chlorine Dioxide: An Alternative to Chlorine?," *Packer Shipper*, Jun. 1996, 4pgs.

"Chlorine Dioxide Use in Fruit and Vegetable Processing" (brochure), Rio Linda Chemical Co., Inc.

"Pride Packaging Co. Tries Chlorine Dioxide," *Hort Expo Northwest*, Dec. 1995, 3 pgs.

Bernarde, M. et al., "Efficiency of Chlorine Dioxide as a Bactericide," Applied Microbiology, Sep. 1965, vol. 13, No. 5 and pp. 776-780.

Carrillo, A. et. al., "Application of Diluted Chlorine Dioxide to Radish and Lettuce Nursuries Insignificantly Reduced Plant Development," Ecotoxicology and Environmental Saftey, 1996, vol. 35 at pp. 57-66.

Chastagner, et. al., "Potential Use of Chlorine Dioxide to Control Diseases in Ornamental Plant Production Systems," Plant Propogators' Society, Sep. 10, 2002, vol. 51 at pp. 275-279.

Chem Fresh, Inc., Oxicide (brochure).

Chlorine Dioxide Disinfection of Produce Washwater, Aeis 653, www.msu.edu/~brook/publications/aeis/aeis653.htm, Jul. 1998. Downloaded Sep. 16, 2011.

Chlorine Dioxide Disinfection of Produce Washwater, Aeis 654, www.msu.edu/~brook/publications/aeis/aeis654.htm, Jul. 1998. Downloaded Sep. 16, 2011.

Guideline No. 15, "Microbiological Control of Food Industry Process Waters: Guidelines on the Use of Chlorine Dioxide and Bromine as Alternatives to Chlorine," Campden & Chorleywood Food Research Association, Jul. 1997. 62 pages.

Gurol, M., "Facts and Myths about Irrigation Water," www.eco-web.com/edi/051201.html, Dec. 2005. Downloaded Sep. 30, 2011.

International Dioxide, Inc., Chlorine Dioxide (brochure).

Irrigation Journal, May/Jun. 1987 "Conditionerigation: New Process Proves Successful," pp. 12-15.

New Jersey Department of Health and Senior Services, Hazardous Substance Fact Sheet, "Chlorine Dioxide," Jun. 1998, rev. Dec. 2005.

Roberts, R., "Integrating Biological Control into Postharvest Disease Management Strategies," HortScience, Jul. 1994, vol. 29, No. 7 at pp. 758-762.

Selectrocide 12G Product Packaging, Rev 5-05A.

Simpson, G., "Biofilm: Removal and Prevention with Chlorine Dioxide," An International Symposium on Chlorine Dioxide: Process Water, Drinking Water and Water Waste Issues, Sep. 14-15, 1995, New Orleans, LA.

Simpson, G. et. al., "A Focus on Chlorine Dioxide: The 'Ideal' Biocide," Unichem International, Inc., Houston, Texas, Jul. 1993.

Spotts, R.A., "Chlorine and Chlorine Dioxide for Control of d'Anjou Pear Decay," Plant Disease, Dec. 1980, vol. 64, No. 12 at pp. 1095-1097.

Steel, "Water Supply and Sewerage," 3$^{rd}$ Ed. pp. 421-437, McGraw-Hill Book Co., Inc. 1953.

Iverson, et. al., "Method of Promoting Unrestricted Flow of Irrigation Water Through Irrigation Networks," Office Action in Ex Parte Reexamination, for Reexamination Control No. 90/011,958, mailed Aug. 17, 2012, 31 pages.

Iverson, et. al., "Method of Promoting Unrestricted Flow of Irrigation Water Through Irrigation Networks," Office Action in Ex Parte Reexamination, for Reexamination Control No. 90/011,958, mailed Mar. 15, 2012, 18 pages.

(56) References Cited

OTHER PUBLICATIONS

Iverson, et. al., "Method of Promoting Unrestricted Flow of Irrigation Wate Through Irrigation Networks," Patent Owner's Response Under 37 CFR 1.111, for Reexamination Control No. 90/011,948, mailed May 15, 2012, 38 pages.
EPA Guidance Manual, Alternative Disinfectants and Oxidants, Chapter 4. Chlorine Dioxide, pp. 4-1-4-41, Apr. 1999. (41 pages).
International Preliminary Examination Report for International Application No. PCT/US95/02128, mailed May 29, 1997, 6 pages.
International Preliminary Examination Report for International Application No. PCT/US01/24457, mailed Nov. 7, 2002, 5 pages.
International Search Report for International Application No. PCT/US95/02128, mailed Jun. 2, 1995, 2 pages.
International Search Report for International Application No. PCT/US01/24457, mailed Dec. 14, 2001, 1 page.
English Language Internet Translation of JP 8-283112, 6 pages.
English Language Internet Translation of JP 9-71502, 8 pages.
Nowack, "Determination of phosphonates in natural waters by ion-pair high-performance liquid chromatography," *Journal of Chromatography A 773* (1-2): 139-146, Jun. 27, 1997. (Abstract).
Nowack, et. al., "Phosphonate Removal During Water Treatment by Adsorption Onto Activated Sludge and Humic Acids," *Preprints of Extended Abstracts 40* (2):622-624, Symposia Papers Presented Before the Division of Environmental Chemistry, American Chemical Society, Washington, DC, Aug. 20-24, 2000 (5 pages).
Written Opinion for International Application No. PCT/US95/02128, mailed Mar. 14, 1997, 4 pages.
Written Opinion for International Application No. PCT/US01/24457, mailed Jul. 12, 2002, 4 pages.
Pitochelli and Mason, Large-Scale Field Applications of Chlorine Dioxide, presented Mar. 21-22, 1994. (14 pages).
Second European Symposium on Chlorine Dioxide and Disinfectants, Paris. Jun. 1999. (10 pages).
Southern Agricultural Insecticides, Inc., 20-20-20 Soluble Fertilizer with Minor Elements Manual; 1998. (1 page).
Vaska and Winston, Evaluation of Alternatives to Gaseous Chlorine for Cooling Water Microbiological Control, presented at the 1992 Cooling Tower Institute Annual Meeting. (14 pages).

\* cited by examiner

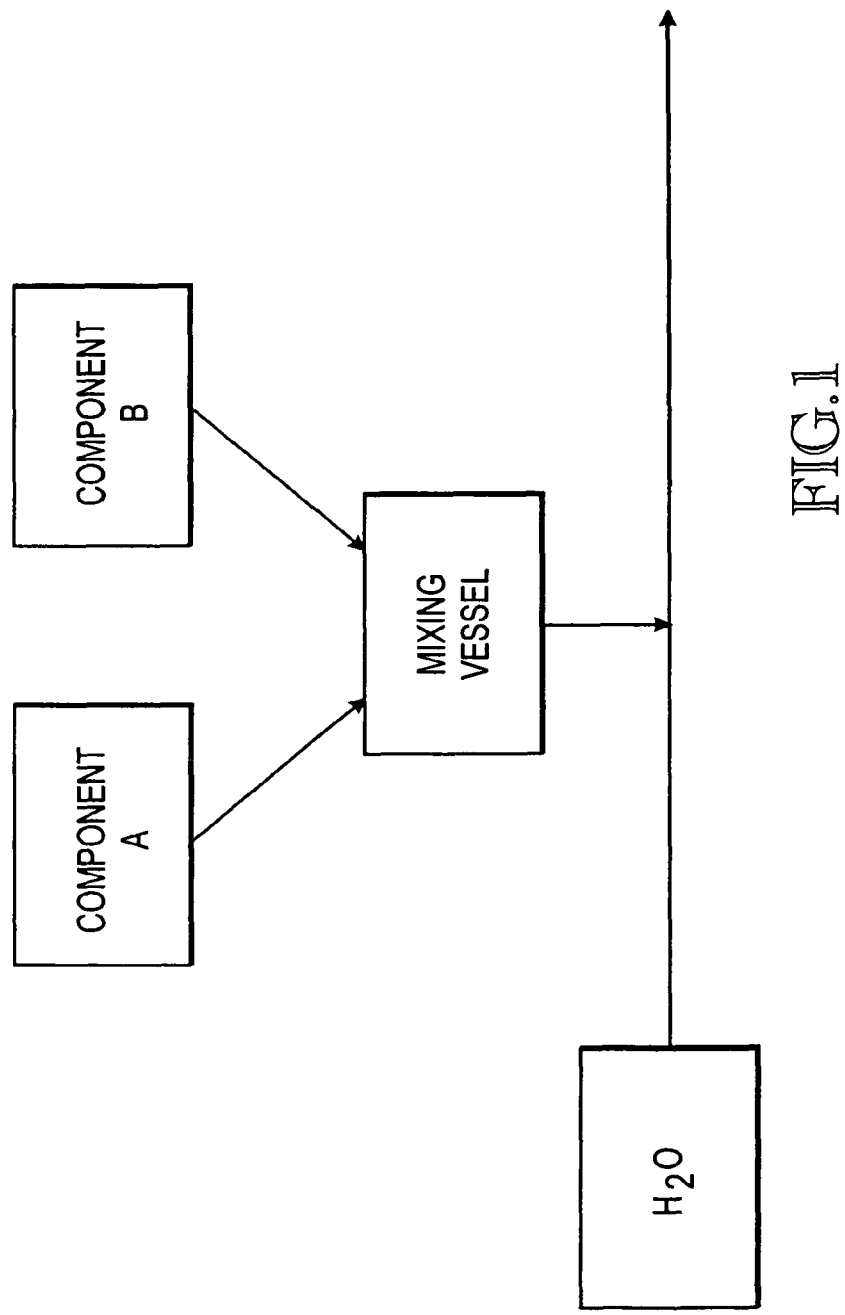

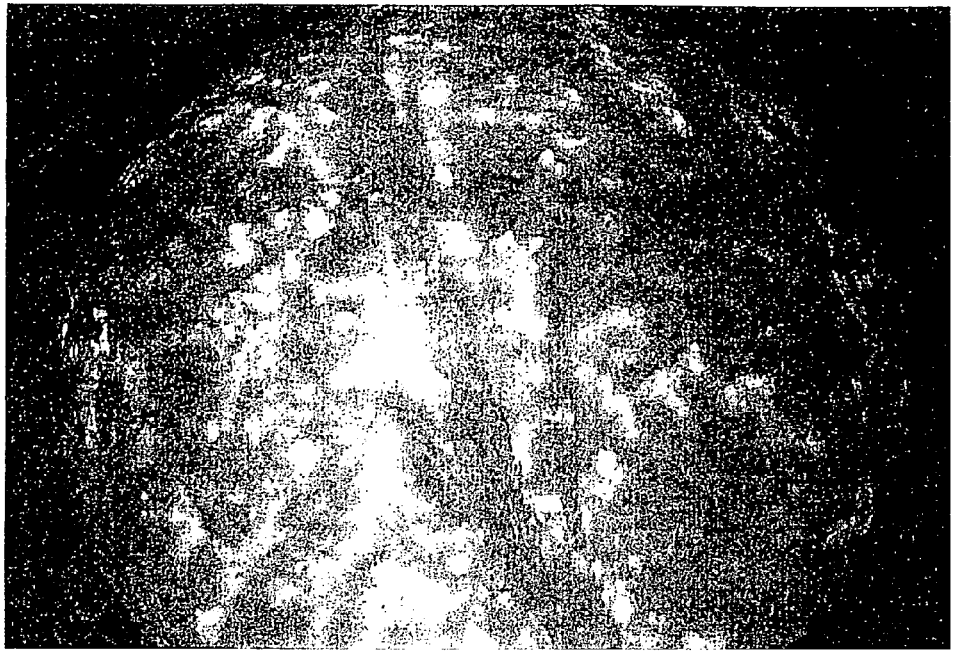
BLANK: 40X1
TREATED: 40X-1

DISINFECTING/MINERAL TREATING COMPOSITION AND METHODS COMPRISING A CHLORITE OR CHLORATE SALT

CROSS-REFERENCE TO RELATED APPLICATION

This application claims priority to U.S. Ser. No. 11/498,495 filed Aug. 2, 2006, which is incorporated by reference herein.

TECHNICAL FIELD

This invention relates to a composition for disinfecting source water and surfaces contacted by the source water, and for substantially eliminating mineral deposits on surfaces. More particularly, it relates to a stable disinfecting/mineral treating composition in water that does not produce dangerous gaseous compounds when mixed with the water.

BACKGROUND OF THE INVENTION

Municipal water, surface water and well water contain varying amounts of pathogens, dissolved oxygen and minerals. The pathogens form biofilms that cause disease and corrosion. Dissolved minerals in the water form crystalline structures that restrict passageways and reduce water flow. There is a need for providing a low cost composition that will effectively eliminate microorganisms and prevent crystalline mineral deposits and that only requires a simple feed of the composition from a container into the source water via an inexpensive metering pump. It is an object of the invention to fill this need.

It is an object of the present invention to reduce or eliminate microorganisms and also prevent crystalline mineral deposits and to do so without generating substantial amounts of chlorine dioxide and/or creating risk of dangerous exothermic and explosive reactions.

Another object of the present invention is to produce an effective composition for reducing or eliminating microorganisms and crystalline mineral deposits without the need for expensive equipment and/or the monitoring and testing of the equipment to assure safe operation.

BRIEF SUMMARY OF THE INVENTION

The composition of the present invention is a disinfectant mineral treatment that causes mineral deposits to become amorphous. The composition is formed by admixing two components in the presence of water. One component is selected from the group consisting of neutralized phosphonate compounds, neutralized phosphonic acid compounds, neutralized derivatives of phosphorus, blends of neutralized phosphonate compounds, neutralized phosphonic acid compounds and neutralized phosphorus derivatives, neutralized anti-scalent polymers, and mixtures thereof. The neutralized phosphonate may be selected from the group consisting of, but not limited to: aminotri(methylene phosphonic acid) (ATMP), 1-hydroxyethylidene-1,1-diphosphonic acid (HEDP), ethylenediamine tetra(methylene phosphonic acid) (EDTMPA), hexamethylenediamine tetra(methylene phosphonic acid) (HMDTMPA), diethylenetriamine penta(methylene phosphonic acid) (DETPMPA), bis(hexamethylenetriamine penta(methylene phosphonic acid)) (BHMPTMPA), 2-phosphonobutane-1,2,4-tricarboxylic acid (PBTC), 2-hydroxy phosphonoacetic acid (HPA), phosphinocarboxylic acid (PCA), nitrilotris(methylene phosphonic acid) (NTMP), and diethylenetriamine penta(methylene phosphonic acid) (DTMP). A preferred neutralized phosphonate is 2 phosphonobutane-1,2,4-tricarboxylic acid (PBTC), and mixtures thereof.

The first component is neutralized to a pH of at least about 7.0 before or after it is admixed with water. Then, a second component, selected from the group comprising chlorite salt and chlorate salt, is admixed to the mixture of the first component and water. The water and the first and second components are present in amounts sufficient to form a stable liquid composition in which there is substantially no conversion of the second component (the salt component) to chlorine dioxide.

After it is made, the composition is stored in containers until used. When used, the composition is pumped out from the container, into source water, using an inexpensive metering pump.

The composition of this invention has a pH of 7.0 or higher. The second component is preferably about a 1% to about a 25% solution of sodium chlorite in water.

A method of the invention involves the use of the composition for converting minerals in the source water to amorphous mineral deposits on surfaces contacted by the source water. The amorphous deposits are easily removed from the surfaces, such as by wiping and/or washing.

Another method of the invention comprises disinfecting source water and surfaces by use of the same two component composition.

These and other advantages and features will become apparent from the detailed description of the best mode for carrying out the invention that follows.

BRIEF DESCRIPTION OF THE DRAWING

FIG. 1 is a flow diagram a water conduit flowing from a source of water, showing a component A being added to the water in the conduit and showing component B being added to the mixture of the water and the component A;

FIG. 2 is a photograph of the "blank" sample taken under a microscope at 40×-1; and FIG. 3 is a photograph of the "treated" sample under the microscope, also at 40×-1.

DETAILED DESCRIPTION OF THE PREFERRED EMBODIMENT

Referring to FIG. 1, a component A and a component B are shown to be mixed together in a mixing vessel. The mixture is then admixed to source water flowing through the conduit 10. Component A is selected from the group consisting of neutralized phosphonate compounds, neutralized phosphonic acid compounds, neutralized derivatives of phosphorus, blends of neutralized phosphonate compounds, neutralized phosphonic acid compounds and neutralized phosphorus derivatives, neutralized anti-scalent polymers, and mixtures thereof. The neutralized phosphonate may be selected from the group consisting of, but not limited to: aminotri(methylene phosphonic acid) (ATMP), 1-hydroxyethylidene-1,1-diphosphonic acid (HEDP), ethylenediamine tetra(methylene phosphonic acid) (EDTMPA), hexamethylenediamine tetra(methylene phosphonic acid) (HMDTMPA), diethylenetriamine penta(methylene phosphonic acid) (DETPMPA), bis(hexamethylenetriamine penta(methylene phosphonic acid)) (BHMPTMPA), 2-phosphonobutane-1,2,4-tricarboxylic acid (PBTC), 2-hydroxy phosphonoacetic acid (HPA), phosphinocarboxylic acid (PCA), nitrilotris(methylene phosphonic acid) (NTMP), and diethylenetriamine penta (methylene phosphonic acid) (DTMP). A preferred neutralized phosphonate is 2 phosphonobutane-1,2,4-tricarboxylic acid (PBTC). Component B is selected from the group comprising chlorite salt and chlorate salt.

One or more of the component A substances may be added to water in a container. The component A is admixed with the water. Component A can be acquired in a dry granular form or in a liquid form. It is important that the mixture of the component A and the water have a pH 7.0 or higher before it and the component B are combined. Component B is a salt and it can be acquired in a dry granular form or in a liquid form. The essential thing is that component A be neutralized so that its pH is at least 7.0 so that when component B the salt compound is added. In the presence of water, the two components A and B and the water will form a stable liquid composition in which there is substantially no conversion of the second component, viz. the chlorite salt or the chlorate salt, to chlorine dioxide.

Another way of preparing the composition is to mix component A with component B and then admix the mixture with water.

Engineered systems that are designed to safely generate chlorine dioxide commonly cost upwards of fifty thousand dollars ($50,000.00) and require routine monitoring and testing to ensure safe operation. According to the invention, the disinfecting/mineral treating composition is simply fed directly from a container to the source water by use of an inexpensive metering pump. Because substantial amounts of chlorine dioxide are not generated in the process, the risk of dangerous exothermic and explosive reactions are eliminated. Because dangerous gaseous compounds are not produced, a safe method of disinfecting and treating minerals in source water is accomplished.

Example #1

Neutralized Phosphonate/Sodium Chlorite Experiment

Collect a sample of pond water or equivalent that is known to contain biological life. Reserve some of the contaminated water to use as a "blank". Add one part neutralized phosphonate chlorite solution to yield 5 ppm $NaClO_2$ and 5.9 ppm PBTC. Tests confirmed residuals. Allow the treated water to sit for approximately 10 minutes before proceeding. Test the blank solution and the treated solution with BTM-2 biological kit and fungi plate; note biological growth over time. On Day 3, the Blank was observed with approximately 10 distinct colonies of bacterial growth; moderate pink on about ½ of agar. There was a lot of mold growth. On Day 3 the treated growth media had no bacterial and no yeast/mold growth.

Example #2

Neutralized Phosphonate/Sodium Chlorite Experiment

Collected two liters of tap water. Calcium chloride and sodium carbonate were added to each liter yielding solutions with approximately 250 ppm hardness. One of the liters was used as a "blank". The other liter was treated with neutralized phosphonate/sodium chlorite solution to yield 5.0 ppm $NaClO_2$ and 5.9 ppm PBTC. Heated the solutions for 10 hours, insuring the water volume did not evaporate below 100 mls.

Remove 1.0 ml of the treated, heated and condensed water and place it on a microscope slide. Allow the sample to dry naturally in the atmosphere. FIG. 2 is a photo of the "blank" sample under the microscope at 40×-1. FIG. 3 is a photo of the "treated" sample under the microscope at 40×-1.

Observations of Dried Blank: This made thick white film on the slide. There are white crystals with "knobs" visible to the naked eye. Under the scope, crystals are dark and rough looking with large dark knobs. The edge of the film had more "snowflake' shaped crystals with knobs.

Observation of Dried sample treated with neutralized phosphonate/sodium chlorite product: This made a thin opaque white film, crystals were long, sparse & thin and they were not agglomerated into a dense structure as the blank was. The conclusion: under identical circumstances, the treated solution had substantially less crystalline substance than the blank solution.

Example #3

Neutralized Phosphonate/Sodium Chlorite Experiment

Collect four liters of tap water. Calcium chloride and sodium carbonate were added to two liters, yielding solutions with approximately 250 ppm hardness. Treat one of the plain tap water and one of the hard water liters with neutralized phosphonate/sodium chlorite solution to yield 5.0 ppm $NaClO_2$ and 5.9 ppm PBTC. Cleanly cut (at an angle) the bottom of 16 fresh rose stems; place four stems into each beaker and observe results over 8 days.

Conclusion

From the information included, we can see the roses treated with neutralized phosphonate/sodium chlorite solution (5.0 ppm $NaClO_2$ and 5.9 ppm PBTC) demonstrated the longest shelf-life. This was particularly visible in hard water since biofilm and hardness mineral crystallization can accumulate in the stems, inhibiting the uptake of water.

| | TAP WATER | |
|---|---|---|
| | Tap-BLANK | Tap-Treated |
| Day 1: Apr. 14, 2006 | 2 yellow, 2 pink; all buds | 2 yellow, 2 pink; all buds |
| Day 2 | Saturday, no observations | Saturday, no observations |
| Day 3 | Sunday, no observations | Sunday, no observations |
| Day 4 | All buds open. 2 pinks w/brown on petals; 1 pink w/dried leaves. | All buds opening & healthy. All leaves green. |
| Day 5 | Same as day 4. | Same as day 4 |
| Day 6 | Same as day 4 | Same as day 4 |
| Day 7 | Same as day 4. Both pinks mostly brown, 1 pink dying. | Same as day 4 |
| Day 8 | 2 yellow are healthy; 2 pink dead. | 3 open & heathy; 1 pink wilting with dried leaves |

| | HARD WATER | |
|---|---|---|
| | Hard-BLANK | Hard-Treated |
| Day 1; Apr. 14, 2006 | 2 pink, 2 yellow. All buds. | 2 pink, 2 yellow. All buds. |
| Day 2 | Saturday, no observations. | Saturday, no observations. |

-continued

| | HARD WATER | |
|---|---|---|
| | Hard-BLANK | Hard-Treated |
| Day 3 | Sunday, no observations. | Sunday, no observations. |
| Day 4 | All open & healthy. 1 yellow has minor blemishes. | All open & healthy. |
| Day 5 | Same as day 4 | Same as day 4 |
| Day 6 | All 4 open & healthy, leaves starting to dry out. | Same as day 4 |
| Day 7 | 1 healthy, 1 wilting yellow. 2 healthy pink. All leaves dried. | Same as day 4, leaves just starting to dry a little. |
| Day 8 | 1 yellow healthy w/dry leves 3 dying w/dried leaves. | All open & healthy, minor leaf drying. |

Observations

| TRIAL # | TREATED, TAP WATER | TREATED, HARD WATER | AVERAGE |
|---|---|---|---|
| BLANK | * | * | worst |
| TREATED | ***** | ***** | best |

* = WORST
***** = BEST

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A method comprising:
 combining a first component and a second component to yield an aqueous composition comprising a mixture of the first component and the second component,
 wherein:
  the first component is an aqueous solution having a pH of at least 7.0 and comprises a phosphorus derivative, and
  the second component is selected from the group consisting of $ClO_2^-$ salts in an aqueous solution or in solid form and $ClO_3^-$ salts in an aqueous solution or in solid form.

2. The method of claim 1, further comprising storing the aqueous composition in a container.

3. The method of claim 2, further comprising removing a portion of the aqueous composition from the container, and combining the portion of the composition with a source water comprising minerals, microorganisms, or a combination thereof.

4. The method of claim 3, wherein the source water is in a conduit.

5. The method of claim 1, further comprising combining a portion of the aqueous composition with a source water comprising minerals, microorganisms, or a combination thereof.

6. The method of claim 5, wherein the source water is in a conduit.

7. The method of claim 1, wherein the aqueous composition is a stable liquid composition.

8. The method of claim 1, wherein the phosphorus derivative is selected from the group consisting of phosphonates and phosphonic acids.

9. The method of claim 1, wherein the phosphorus derivative is selected from the group consisting of aminotri(methylene phosphonic acid) (ATMP), 1-hydroxyethylidene-1,1-diphosphonic acid (HEDP), ethylenediamine tetra(methylene phosphonic acid) (EDTMPA), hexamethylenediamine tetra(methylene phosphonic acid) (HMDTMPA), diethylenetriamine penta(methylene phosphonic acid) (DETPMPA), bis(hexamethylenetriamine penta(methylene phosphonic acid)) (BHMPTMPA), 2-phosphonobutane-1,2,4-tricarboxylic acid (PBTC), 2-hydroxy phosphonoacetic acid (HPA), phosphinocarboxylic acid (PCA), nitrilotris(methylene phosphonic acid) (NTMP), and diethylenetriamine penta(methylene phosphonic acid) (DTMP).

10. The method of claim 1, wherein the second component in the mixture undergoes substantially no conversion to chlorine dioxide.

11. A method comprising:
 flowing source water through a conduit; and
 combining an aqueous composition comprising a mixture of a first component and a second component with the source water in the conduit,
 wherein the aqueous composition is formed by a process comprising combining the first component and the second component, wherein the first component is an aqueous solution having a pH of at least 7.0 and comprises a phosphorus derivative, and the second component is selected from the group consisting of $ClO_2^-$ salts in an aqueous solution or in solid form and $ClO_3^-$ salts in an aqueous solution or in solid form.

12. The method of claim 11, wherein the source water comprises minerals, microorganisms, or a combination thereof.

13. The method of claim 11, wherein the second component in the mixture undergoes substantially no conversion to chlorine dioxide.

14. A method comprising:
 combining an aqueous composition comprising a mixture of a first component and a second component with water comprising minerals, microorganisms, or a combination thereof, to yield a treated water,
 wherein the aqueous composition is formed by a process comprising combining the first component and the second component, wherein the first component is an aqueous solution having a pH of at least 7.0 and comprises a phosphorus derivative, and the second component is selected from the group consisting of $ClO_2^-$ salts in an aqueous solution or in solid form and $ClO_3^-$ salts in an aqueous solution or in solid form.

15. The method of claim 14, wherein the aqueous composition converts minerals in the water to amorphous mineral deposits on surfaces contacted by the water during evaporation of the treated water.

16. The method of claim 14, wherein the water comprises minerals, and crystalline mineral deposits formed during evaporation of the treated water are non-agglomerated.

17. The method of claim 14, wherein the water comprises microorganisms, and the composition inhibits growth of the microorganisms.

18. The method of claim 14, wherein the second component in the mixture undergoes substantially no conversion to chlorine dioxide.

19. The method of claim 1, wherein the pH of the aqueous composition is at least 7.0.

20. The method of claim 11, wherein the pH of the aqueous composition is at least 7.0.

21. The method of claim 14, wherein the pH of the aqueous composition is at least 7.0.

* * * * *